(12) United States Patent
Simpson et al.

(10) Patent No.: US 8,658,415 B2
(45) Date of Patent: Feb. 25, 2014

(54) METHODS OF SUSTAINING CULTURE VIABILITY

(71) Applicant: LanzaTech New Zealand Limited, Roselle, IL (US)

(72) Inventors: Sean Dennis Simpson, Auckland (NZ); Christophe Collet, Auckland (NZ); Bakir Al-Sinawi, Auckland (NZ)

(73) Assignee: Lanza Tech New Zealand Limited, Auckland (NZ)

(*) Notice: Subject to any disclaimer, the term of this patent is extended or adjusted under 35 U.S.C. 154(b) by 0 days.

(21) Appl. No.: 13/684,215

(22) Filed: Nov. 22, 2012

(65) Prior Publication Data

US 2013/0084559 A1    Apr. 4, 2013

Related U.S. Application Data

(63) Continuation of application No. 13/060,334, filed as application No. PCT/NZ2010/000029 on Feb. 23, 2010, now abandoned.

(60) Provisional application No. 61/155,870, filed on Feb. 26, 2009.

(51) Int. Cl.
*C12N 1/04* (2006.01)
*C12N 1/20* (2006.01)

(52) U.S. Cl.
USPC ........................................ 435/260; 435/252.1

(58) Field of Classification Search
None
See application file for complete search history.

(56) References Cited

U.S. PATENT DOCUMENTS

| | | | |
|---|---|---|---|
| 4,605,620 A | 8/1986 | Andersch et al. | |
| 5,063,156 A | 11/1991 | Glassner et al. | |
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Gaddy et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,753,170 B2 | 6/2004 | Gaddy et al. | |
| RE39,175 E | 7/2006 | Gaddy et al. | |
| 7,196,218 B2 | 3/2007 | Gaddy et al. | |
| 7,285,402 B2 | 10/2007 | Gaddy et al. | |
| 7,704,723 B2 | 4/2010 | Huhnke et al. | |
| 2007/0275447 A1 | 11/2007 | Lewis et al. | |
| 2010/0323417 A1 | 12/2010 | Simpson et al. | |

FOREIGN PATENT DOCUMENTS

| WO | 2008/028055 | 3/2008 |
|---|---|---|
| WO | 2008/137402 | 11/2008 |
| WO | 2008/154301 | 12/2008 |
| WO | 2009/020747 | 2/2009 |
| WO | 2009/022925 | 2/2009 |
| WO | 2009/058028 | 5/2009 |
| WO | 2009/1058028 | 5/2009 |
| WO | 2009/113878 | 9/2009 |
| WO | 2010/064932 | 6/2010 |
| WO | 2010/064933 | 6/2010 |
| WO | 2010/093262 | 8/2010 |
| WO | 2011/002318 | 1/2011 |

OTHER PUBLICATIONS

Oelgeschlager, E, et al, "Carbon monoxide-dependent energy metabolism in anaerobic bacteria and archaea" Archives of Microbiology. 2008 vol. 190, No. 3, pp. 257-269.
ATCC Catalogue. ATCC Bacteria and Bacteriophages. 19th edition. 1996, pp. 3, 166, 213, 222 and 467.
ZhongbinWei, Study on the Viable But Nonculturable State *Lactobacillus lactis*, China Master Thesis Agricultural Science and Technology Series, D050-14, : Table 2-1 on p. 16, Section 2.1 from bottom of p. 19 to top of p. 22, Section 4.1 on p. 30, Section 1.5.5 on p. 33 and lines 1-2 on p. 36 (Apr. 18, 2008).
CAPLUS Accession No. 1937:49061; Henry, B.S. et al; "Studies of yeast and the fermentation of fruits and berries of Washington"; Bulletin of the University of Washington, 1936, 90pp.
Georgieva, T.I et al; "Effect of temperature on ethanol tolerance o a thermophilic anaerobic ethanol producer *Thermoanaerobacter* A10: Modeling and Simulation", Biotechnology and Bioengineering, 2007, vol. 98, No. 6, pp. 1161-1170.
Phillips, JR, Clausen, EC & Gaddy, JL (1994). Synthesis gas as substrate for the biological production of fuels and chemicals. Applied biochemistry and biotechnology, 45(1), 145-157.
Abrini, J et al. 1994, *Clostridium autoethanogenum*, sp. Nov., an anaerobic bacterium that produces ethanol from carbon monoxide. Archives of Microbiology 161(4), 345-351.
Ragsdale, SW 2004, Life with carbon monoxide. Critical reviews in biochemistry and molecular biology, 39(3), 165-195.
Henstra et al, 2007, Microbiology of synthesis gas fermentation for biofuel production. Current opinion in biotechnology, 18(3), 200-206.
Hilliard, CM et al, "The germicidal action of freezing temperatures upon bacteria", The journal of bacteriology, 1918 vol. 3, No. 4, pp. 423-431.
Doyle, E. "Survival and growth of bacterial pathogens on raw meat during chilling", Food research institute, Feb. 2002 (retrieved Jul. 9, 2010), retrieved from internet URL: http://www.amif.org/ht/a/GetDocumentAction/i/7436 (see introduction).
Yakult Australia (retrieved Jul. 8, 2010) retrieved from URL: http://web.archive.org/web/20080719152510/http://yakult.com.au/faqs01.htm Published on Jul. 19, 2008 as per the Wayback Engine.

*Primary Examiner* — Vera Afremova
(74) *Attorney, Agent, or Firm* — Frank S Molinaro

(57) ABSTRACT

The present invention relates to methods for sustaining a microbial culture during periods of limited substrate supply. In accordance with the methods of the invention, a microbial culture comprising carboxydotrophic bacteria can be sustained during periods of limited substrate supply by maintaining the temperature of the microbial culture at a temperature below an optimum operating temperature. Examples of periods of limited substrate supply include when the microbial culture is transported to a remote location or during time when it is stored.

20 Claims, 1 Drawing Sheet

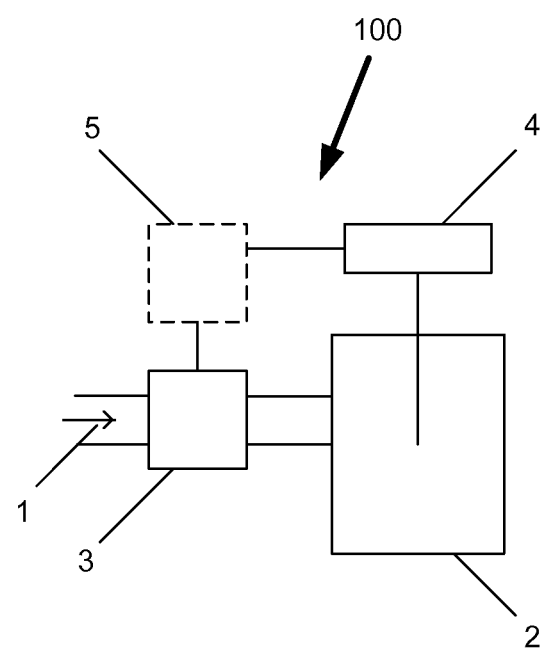

METHODS OF SUSTAINING CULTURE VIABILITY

CROSS REFERENCE TO RELATED APPLICATIONS

This application is a continuation of pending U.S. application Ser. No. 13/060,334 which in turn is a National Stage of International Application No. PCT/NZ2010/000029, filed on Feb. 23, 2010, which claims the benefit of the priority date of U.S. Provisional Application No. 61/155,870, filed Feb. 26, 2009. The content of all of which applications mentioned above are incorporated herein by reference in their entirety.

FIELD OF THE INVENTION

This invention relates generally to methods for increasing the efficiency of microbial growth and production of products by microbial fermentation on gaseous substrates. More particularly the invention relates to processes for producing products such as alcohols by microbial fermentation before, during and/or after a substrate stream comprising CO becomes limited. In particular embodiments, the invention relates to methods of sustaining viability of a microbial culture during periods of limited substrate comprising CO.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Several enzymes known to be associated with the ability of micro-organisms to use carbon monoxide as their sole source of carbon and energy are known to require metal co-factors for their activity. Examples of key enzymes requiring metal cofactor binding for activity include carbon monoxide dehydrogenase (CODH), and acetyl-CoA synthase (ACS).

WO2007/117157 and WO2008/115080, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process.

The fermentation of gaseous substrates comprising CO, to produce products such as acids and alcohols, typically favours acid production. Alcohol productivity can be enhanced by methods known in the art, such as methods described in WO2007/117157, WO2008/115080, WO2009/022925 and WO2009/064200, which are fully incorporated herein by reference.

In order to sustain viability of one or more carboxydotrophic bacteria, such as acetogenic bacteria, a substantially continuous substrate stream comprising sufficient quantities of CO must be made available to the microbial culture. Accordingly, if a sufficient amount of CO (or $CO_2$/$H_2$) is not made available to the microbial culture, the culture may deteriorate and ultimately die. For example during times of insufficient CO supply, such as periods of storage, limited substrate supply or culture/inoculum transfer, a microbial culture will rapidly deplete the available CO and viability will deteriorate.

WO2009/114127 provides a method of sustaining viability of microorganisms during periods of limited substrate supply. However, the method includes adding CO2 to the bioreactor wherein a significant amount of ethanol is converted into acetate, resulting in a decrease in pH. This effect needs to be counteracted to prevent inhibition by excess molecular acetic acid.

It is an object of the present invention to provide a process that goes at least some way towards overcoming the above disadvantages, or at least to provide the public with a useful choice.

SUMMARY OF THE INVENTION

In a particular aspect of the invention, there is provided a method of sustaining viability of a microbial culture of carboxydotrophic bacteria, wherein a substrate comprising CO is limited or unavailable, the method comprising the step of maintaining the culture at a temperature or within a temperature range below the optimum operating temperature for growth and/or product production of the microbial culture.

In particular embodiments, the microbial culture is suspended in a liquid nutrient medium.

A substrate is considered to be limited when there is insufficient CO available to sustain growth and/or metabolite production by the microbial culture. For example in a continuous culture, the substrate is considered to be limited when steady state growth cannot be sustained.

Typically, the substrate comprising CO is consumed by a microbial culture at a rate of at least 0.1 mmol/g microbial cells/minute; or at least 0.2 mmol/g/minute; or at least 0.3 mmol/g/minute; or at least 0.4 mmol/g/minute; or at least 0.5 mmol/g/minute. As such, in particular embodiments, the substrate comprising CO is limited if less than at least 0.1 mmol/g microbial cells/minute; or at least 0.2 mmol/g/minute; or at least 0.3 mmol/g/minute; or at least 0.4 mmol/g/minute; or at least 0.5 mmol/g/minute is available to the microbial culture. Limitation of the substrate is typically associated with a cessation or slowing of growth of the micro-organism.

In certain embodiments of the invention, the temperature of the microbial culture is reduced to at least 5°; or at least 10°; or at least 15°; or at least 20°; or at least 25°; or at least 30° below the optimum operating temperature of the microbial culture. Those skilled in the art will appreciate upon consideration of the instant disclosure the optimum operating temperature of a carboxydotrophic bacteria. However, by way of example, *Clostridium autoethanogenum* has an optimum operating temperature of 37° C. As such, in particular embodiments of the invention, the temperature of the microbial culture is reduced to less than 32° C., or less than 30° C., or less than 25° C., or less than 20° C., or less than 15° C., or less than 10° C., or less than 5° C.

In particular embodiments of the invention, the temperature of the microbial culture can be reduced by cooling the liquid nutrient medium directly or indirectly. In particular embodiments, at least a portion of the liquid nutrient medium may be passed through a heat exchanging means to cool the liquid. Additionally, or alternatively, the microbial culture is contained within a vessel such as a bioreactor or a transport vessel, and the vessel can be cooled by any known cooling means, such as a cooling jacket.

In particular embodiments, the viability of the microbial culture can be substantially maintained at reduced temperature for at least 3 h, or at least 5 h, or at least 7 h, or at least 15 h, or at least 30 h, or at least 48 h.

In another aspect of the invention, there is provided a method of storing a microbial culture of a carboxydotrophic bacteria, wherein a substrate stream is limited or unavailable, the method comprising the step of reducing the temperature of the microbial culture below the optimum operating temperature.

In particular embodiments, following storage, for example when a substrate stream comprising sufficient CO is restored, the temperature of the microbial culture is increased to the optimum operating temperature. In such embodiments, the viability of the microbial culture is substantially sustained throughout cooling, storage and warming.

In another aspect, there is provided a method of sustaining viability of a microbial culture during storage, the method including the steps of:

cooling the microbial culture to a temperature or temperature range below the optimum operating temperature, storing the microbial culture for a period of time, In particular embodiments, the method includes warming the culture to the optimum operating temperature following storage.

In particular embodiments, the extended period is at least 3 h, or at least 5 h, or at least 7 h, or at least 15 h, or at least 30 h, or at least 48 h.

In particular embodiments, the method is used to sustain viability of a culture during periods of limited CO supply. In another embodiment, the method can be used to sustain viability of a microbial culture during transport to a remote location. In such embodiments, it is considered there may be an insufficient CO supply and/or inadequate agitation to sustain viability. As such, cooling the microbial culture sustains viability for an extended period.

In particular embodiments of the preceding aspects, storage of the culture includes embodiments wherein the culture is maintained in a bioreactor under limited substrate conditions. Additionally or alternatively, the culture can be transferred from a bioreactor to a storage vessel and/or transport vessel. It is expected that in such embodiments, the culture can be returned to a bioreactor at a later time.

In particular embodiments, the microbial culture can be used to inoculate a bioreactor following storage. In such embodiments, the microbial culture may be warmed to the optimum operating temperature prior to, during or after inoculation.

In another aspect of the invention, there is provided a method of transporting an inoculum comprising a microbial culture of carboxydotrophic bacteria, the method including:

cooling the microbial culture to below the optimum operating temperature, transporting the microbial culture to a remote location, inoculating a bioreactor with the microbial culture.

In particular embodiments, the microbial culture is transported to a remote location in a transport vessel. In particular embodiments, the microbial culture can be cooled and/or warmed in the transport vessel.

In particular embodiments, the method included pressurising the transport vessel with a substrate comprising CO. In particular embodiments, the transport vessel includes mixing means.

Embodiments of the invention find particular application in the production of acids and alcohols, such as ethanol by fermentation of a gaseous substrate comprising CO. The substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment of the invention, the gaseous substrate is syngas. In one embodiment, the gaseous substrate comprises a gas obtained from a steel mill.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In various embodiments, the fermentation is carried out using a culture of one or more strains of carboxydotrophic bacteria. In various embodiments, the carboxydotrophic bacterium is selected from *Clostridium, Moorella, Oxobacter, Peptostreptococcus, Acetobacterium, Eubacterium* or *Butyribacterium*. In one embodiment, the carboxydotrophic bacterium is *Clostridium autoethanogenum*.

The methods of the invention can be used to produce any of a variety of alcohols, including without limitation ethanol and/or butanol, by anaerobic fermentation of acids in the presence of substrates, particularly gaseous substrates containing carbon monoxide. The methods of the invention can also be applied to aerobic fermentations, to anaerobic or aerobic fermentations of other products, including but not limited to isopropanol, and to fermentation of substrates other than carbon containing gases.

In another aspect, there is provided a system for fermentation of a substrate comprising CO, including at least one bioreactor; determining means adapted to determine whether the substrate comprising CO is provided to a microbial culture is limited or non-limited; and temperature control means configured such that, in use, the temperature of the bioreactor can be adjusted in response to determination of whether the supply of the substrate comprising CO to the microbial culture is limited or non-limited.

In particular embodiments, the controlling means are configured to reduce the temperature of the bioreactor if the determining means determines the supply of the substrate comprising CO is limited. In particular embodiments, the system includes processing means configured such that the temperature of the bioreactor can be automatically regulated in response to changes in whether the substrate comprising CO is limited or non-limited.

In another embodiment, the temperature control mean is configured such that the temperature of the bioreactor can be maintained at or about the optimum operating temperature if the substrate is not limiting.

The invention may also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

In accordance with the methods of the invention, it has been surprisingly recognised that carboxydotrophic microbial cultures may be stored with minimal or no additional substrate feeding and/or agitation, at temperatures below their optimum. Accordingly, in particular embodiments, the microbial culture can be transported from one location to a remote location at temperatures substantially below their growth and/or metabolite production optimum temperature, and may be subsequently used to inoculate a bioreactor. Typically, when a carboxydotrophic microbial culture is stored without providing additional substrate and/or agitation, the microbial culture will rapidly deplete any CO dissolved in a liquid nutrient medium and viability of the culture deteriorates over time. Consequently, when such cultures are used to inoculate a bioreactor following storage without agitation, there may be a lag time before microbial growth and/or expected productivity is observed and/or the inoculation may be unsuccessful.

Additionally or alternatively, in particular embodiments, where a substrate comprising CO, for example a gaseous substrate stream, is not continuously available, the microbial culture can be cooled to a temperature below the optimum operating temperature and stored until further substrate is available. In other embodiments where the substrate is limited (i.e. where CO is available but not enough to promote optimum growth and/or metabolite production), the microbial culture may be cooled to reduce the requirement for CO.

In accordance with particular embodiments of the invention, the method can be used to sustain viability of a microbial culture through periods of limited substrate supply. For example, continuous steady state fermentation of a substrate comprising CO typically requires the substrate to be provided in a non-limited manner such that a substantially constant growth and metabolite production rate is sustained. However, the methods of the invention can be used to sustain the viability of the culture during periods of limited substrate supply which would otherwise result in culture deterioration.

Without wishing to be bound by theory, in order to sustain viability of carboxydotrophic bacteria such as *Clostridium autoethanogenum*, CO needs to be supplied to the culture at a rate greater than or equal to the CO uptake rate of the microbial culture. For example, under optimum conditions required to promote growth and/or metabolite production, the CO uptake rate of the microbial culture is at least 0.1 mmol/g microbial cells/minute; or at least 0.2 mmol/g/minute; or at least 0.3 mmol/g/minute; or at least 0.4 mmol/g/minute; or at least 0.5 mmol/g/minute. Accordingly, in particular embodiments where a microbial culture is suspended in a liquid nutrient medium, the culture will rapidly deplete CO dissolved in the medium unless the dissolved CO can be replenished at a rate equal to or faster than the CO uptake rate. Since CO is poorly soluble in aqueous nutrient media, an external force, such as agitation and/or elevated pressure, is typically required in addition to a constant supply of a substrate comprising CO to maintain desirable CO transfer rate into solution. In bioreactors, this is typically achieved by sparging CO into the liquid nutrient medium and optionally further agitating the liquid to increase the rate of CO transfer into the liquid. Such methods are not generally available in vessels suitable for storage of a microbial culture in a liquid nutrient medium, such as a transport vessel.

It is recognised that in particular embodiments, wherein the microbial culture is being transported from one location to a remote location, there may be a small degree of agitation through movement of the vessel. However, it is considered that the minor agitation associated with vessel transport (i.e. transport by road) is substantially less than what is required to maintain a CO transfer rate into the liquid nutrient medium to prevent culture deterioration.

In accordance with the methods of the invention, cooling the microbial culture substantially sustains the viability of the culture over an extended period. In particular embodiments, the depletion of CO in a storage vessel can be minimised by cooling the vessel. Additionally or alternatively, the microbial culture may be allowed to cool towards a lower ambient temperature. Accordingly, when such cultures are optionally returned to an optimum temperature (or an optimum temperature range) and used to inoculate a bioreactor following storage, microbial growth and/or desired productivity is observed more quickly. Such methods ameliorate or at least reduce the need for additional CO, sparging and/or agitation.

DEFINITIONS

Unless otherwise defined, the following terms as used throughout this specification are defined as follows:

The term "substrate comprising carbon monoxide" and like terms should be understood to include any substrate in which carbon monoxide is available to one or more strains of bacteria for growth and/or fermentation, for example.

"Gaseous substrate comprising carbon monoxide" include any gas which contains carbon monoxide. The gaseous substrate will typically contain a significant proportion of CO, preferably at least about 5% to about 100% CO by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

Unless the context requires otherwise, the phrases "storage" and "store" are used in reference to periods when a microbial culture has a limited substrate supply or a substrate is unavailable. As such, the term includes periods when a microbial culture under steady state growth conditions is temporarily unavailable limited in substrate supply and includes periods when a microbial culture is transferred from a bioreactor into a storage vessel, such as an inoculum transfer vessel.

The term "overall net conversion" and the like, as used herein, is intended to describe the conversion of substrates, such as CO, to products including acid(s) and/or alcohol(s) by a microbial culture at a particular time point. It is recognised that portions of a microbial culture may be devoted to different functions at a particular time point and a number of products may be produced. Furthermore, one or more of the products present in the fermentation broth may be converted into other products. Accordingly, the overall net conversion includes all the products produced by the microbial culture at any particular point in time.

While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol, and butanol. The methods may also be of use in producing hydrogen. By way of example, these products may be produced by fermentation using microbes from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates such as automobile exhaust gases and high volume CO-containing industrial flue gases.

Fermentation

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium* ragsdalei (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The substrate may be a CO-containing waste gas obtained as a by-product of an industrial process, or from some another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 60% to 90% CO by volume, and from 70% to 90% CO by volume. In particular embodiments, the substrate comprises 25%, or 30%, or 35%, or 40%, or 45%, or 50% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Sustaining Culture Viability

In accordance with the invention, there is provided a method of substantially sustaining viability of a microbial culture of carboxydotrophic bacteria, wherein substrate comprising CO is limited or unavailable, the method comprising reducing the temperature of the microbial culture below the optimum temperature for growth and/or product production.

In accordance with the methods of the invention, culture viability is sustained if, on warming to optimum temperature (or range), the culture can resume metabolism to produce products and/or cell growth. In particular embodiments, the microbial culture can be used to inoculate a bioreactor and sustaining culture viability ensures the culture can resume metabolism following transfer. It is recognised that a microbial culture stored in accordance with the methods of the invention may continue to metabolise and/or grow albeit at a slower rate. However, on restoring the temperature of the microbial culture toward the optimum, metabolism and/or growth rate are expected to increase to pre-storage levels.

A microbial culture becomes limited in CO when the rate of transfer of CO into an aqueous nutrient medium is slower than the rate at which the microbial culture can take up (or consume) the CO. Typically, carboxydotrophic bacteria, such as *Clostridium autoethanogenum*, uptake CO from a liquid nutrient medium at a rate greater than 0.1 mmol/g microbial cells/minute; or at least 0.2 mmol/g/minute; or at least 0.3 mmol/g/minute; or at least 0.4 mmol/g/minute; or at least 0.5 mmol/g/minute. Accordingly, it is generally necessary to provide a constant stream of a substrate comprising CO to the microbial culture. Furthermore, due to the low solubility of CO in aqueous systems, it is typically necessary to further increase the CO transfer rates (mass transfer), for example by increasing partial pressure of CO in the substrate stream and/or agitation of the liquid nutrient medium. Upon consideration of the instant disclosure, those skilled in the art will appreciate alternative methods of increasing mass transfer of CO in accordance with particular embodiments of the invention.

In particular embodiments, the methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough. Unless the microbial culture is cooled in accordance with the methods of the invention, the viability of the microbial culture will diminish over time, resulting in complete culture death, or the culture deteriorating to such a level where it is no longer limited by the conditions.

For example, in particular embodiments, a microbial culture comprising one or more carboxydotrophic micro-organisms can be operated under substantially steady state conditions when a substrate comprising CO is not limited. Under such conditions, it is expected the microbial culture will have a substantially constant growth rate and substantially constant metabolite(s) production rate. However, when the substrate cannot be provided in a non-limited way, microbial growth will slow or cease and the microbial culture will rapidly deteriorate and will wash out of a continuously purged bioreactor. Under such conditions, even if the substrate is returned to a non-limited supply, the culture may not be revived, or at least revival takes an extended period. However, in accordance with the invention, the temperature of the culture is decreased, such that viability of the microbial culture is sustained during storage periods of limited or no substrate supply.

It is recognised that the metabolism of the microbial culture may slow when the temperature is decreased, so operating conditions, such as cell retention times may need to be adjusted.

In particular embodiments of the invention, the stored microbial culture is used for inoculation of a bioreactor. In such embodiments, it is desirable that the culture is suitably dense (i.e. large number of microbes per unit volume) and that the viability of the culture is substantially sustained during storage (i.e. transport to a remote location). Typically, the higher the density of the microbial cells in the culture, the faster they will deplete any CO available in a liquid nutrient medium. Without wishing to be bound by theory, it is considered that when CO is not available, or is sufficiently depleted, the viability of the microbial culture decreases. For example, at least a portion of the culture begins to die off and/or the culture switches to a slower metabolism, such that when a bioreactor is inoculated with the microbial culture, there is a lag before high growth rates and/or productivity is attained. However, when the culture is cooled, the depletion of CO in the liquid nutrient medium is slowed such that the culture viability is substantially preserved over an extended period.

In accordance with the methods of the invention, the culture may be cooled to a temperature below the optimum growth and/or metabolite production temperature, such that viability of the culture is sustained over an extended period. Typically, carboxydotrophic micro-organisms have an optimum operating temperatures of carboxydotrophic bacteria in the range 30-70° C. Examples of optimum operating temperature are detailed in "Microbiology of synthesis gas fermentation for biofuels production" A. M. Henstra et al. Current Opinion in Biotechnology, 2007, 18, 200-206. For example, mesophilic bacteria, such as *Clostridium autoethanogenum, Clostridium ljungdahlii* and *Clostridium carboxydivorans* have an optimum growth and metabolite production temperature of approximately 37° C. However, thermophilic bacteria have significantly higher optimum temperatures of 55-70° C., for example strains of *Moorella thermoacetica* (55-60° C.), *Carboxydothermus hydrogenoformans* (70-72° C.), *Desulfotomaculum carboxydivorans* (60° C.). As such, in accordance with the methods of the invention, it is necessary to cool the microbial culture to at least 2°; or at least 5°; or at least 10°; at least 15°; or at least 20°; or at least 25°; or at least 30° below the optimum temperature to sustain culture viability. For example, *Clostridium autoethanogenum* can be cooled to less than 30° C., or less than 25° C., or less than 20° C., or less than 15° C., or less than 10° C., or less than 5° C.

In accordance with the methods of the invention, on cooling, viability of the culture is sustained for extended periods, even in the absence of additional substrate comprising CO and/or agitation. In particular embodiments, viability of the culture is sustained for at least 3 h, or at least 5 h, or at least 7 h, or at least 15 h, or at least 30 h, or at least 48 h. For example, *Clostridium autoethanogenum* remains viable for at least 30 hours, when stored at reduced temperature.

Those skilled in the art will appreciate means required to cool a microbial culture will depend on several factors including size and shape of the vessel containing the culture, speed at which the culture is cooled and whether the culture is exothermic or endothermic. For example, many large scale fermentation processes need to be externally cooled to remove excess heat generated during the fermentation reaction. The known cooling means already provided may be adapted to further cool the microbial culture to sustain viability. In alternative embodiments, where the microbial culture requires external heating to maintain the optimum operating temperature, the culture may be cooled by removing the heat source and allowing the fermenter to cool to ambient temperature over time. Additionally or alternatively, such cultures may be further cooled using any known refrigeration or cooling means.

In particular embodiments of the invention, the liquid nutrient media is allowed to cool below the optimum operating temperature by removing thermostatic heat control. Under such conditions, the temperature of the liquid nutrient media and the microbial culture will fall toward ambient temperature over time. In accordance with the invention, as the temperature of the microbial culture falls below the optimum operating temperature, alcohol productivity increases.

It is considered that periods where viability of a microbial culture may be sustained using the methods of the invention will be commonly encountered in industrial fermentation processes, as continuity of a substrate stream comprising CO may not be guaranteed. For example, where a substrate comprising CO is derived from an industrial process, such as off-gas from a steel mill, there may be occasions where the industrial process (i.e. steel manufacture) is slowed or shut down for extended periods. Under such conditions, the production of a substrate comprising CO will slow or stop altogether. Consequently, when CO supply is limited or CO is unavailable to a bioreactor containing a carboxydotrophic microbial culture, the viability of the culture will diminish over time. However, in accordance with the methods of the invention, if the culture is cooled, the viability can be sustained during CO limited operation.

Similarly, when syngas produced from the gasification of feedstock's such as biomass or municipal solid waste is used as the substrate stream, there may be times when the CO content of the stream decreases, or the gasifier has to be taken off-line, for maintenance (for example). Again, under such conditions, viability of a microbial culture requiring CO for metabolism will deteriorate unless the culture can be cooled in accordance with the methods of the invention.

In an alternative embodiment, the methods of the invention can be used to substantially sustain the viability of a microbial culture used for inoculation of a remote bioreactor. For example, a microbial culture can be placed in a vessel suitable for transport and transported to a remote location. Typically, the transport vessel would require a supply of CO and agitation means to ensure viability of the culture was sustained, both of which can be difficult to provide in mobile environments. However, in accordance with the methods of the invention, the microbial culture can be cooled in the transport vessel such that viability of the inoculum is sustained during transport, even in the absence of a sufficient supply of CO and/or agitation.

In accordance with another embodiment of the invention, there is provided a system for fermentation of a substrate comprising CO, including at least one bioreactor; determining means adapted to determine whether the substrate comprising CO is provided to a microbial culture is limited or non-limited; and temperature control means configured such that, in use, the temperature of the bioreactor can be adjusted in response to determination of whether the supply of the substrate comprising CO to the microbial culture is limited or non-limited.

In particular embodiments, wherein the determining means determine that the substrate supply has become limited, the temperature of the microbial culture can be decreased to sustain culture viability. Additionally or alternatively, wherein the determining means determines the substrate is not limited, the temperature can be maintained substantially at optimum operating temperature. In particular embodiments, the system includes processing means, such that in use, the controlling means can regulate the temperature of the microbial culture automatically in accordance with the methods of the invention.

FIG. 1 is a schematic representation of a system 100 according to one embodiments of the invention. Input substrate stream 1 enters bioreactor 2 via a suitable conduit. Input substrate stream 1 comprises CO and in accordance with the methods of the invention, the rate of supply and/or the composition of the substrate stream 1 may vary. The system 100 includes determining means 3 which, in use, determine whether the substrate supplied to a microbial culture in the bioreactor is limited. The system 100 includes temperature control means 4, which can regulate the temperature of the bioreactor 1 such that a microbial culture can be maintained at an optimum operating temperature, or the temperature decreased and/or maintained at a temperature below the optimum operating temperature.

In particular embodiments, the temperature control means 4 is configured such that in use, if the determining means determines the substrate supply is not limited, the temperature of the fermentation can be maintained at or around the optimum operating temperature. Additionally or alternatively, if the determining means 3 determines that the substrate supply is limited, the controlling means 4 can decrease the temperature of the bioreactor 1 in accordance with the methods of the invention. Thus, the temperature can be controlled at a temperature substantially below the optimum operating temperature until the substrate supply is no longer limiting.

In particular embodiments, the system 100 includes optional processing means 5 configured to regulate the controlling means 4 automatically, in response to determinations made by the determining means 3.

EXAMPLES

Materials and Methods
Preparation of Media LM33:

| Media Component | Concentration per 1.0 L of Media |
|---|---|
| $MgCl_2 \cdot 6H_2O$ | 0.5 g |
| NaCl | 0.2 g |
| $CaCl_2 \cdot 6H_2O$ | 0.26 g |
| $NaH_2PO_4$ | 2.04 g |
| KCl | 0.15 g |
| $NH_4Cl$ | 2.5 g |
| Composite trace metal solution (LS06) | 10 mL |
| Composite B vitamin solution (LS03) | 10 mL |
| Resazurin (2 g/L stock) | 1 mL |

-continued

| Media Component | Concentration per 1.0 L of Media |
|---|---|
| FeCl$_3$ (5 g/L stock) | 2 mL |
| Cysteine HCl | 0.5 g |
| Distilled water | Up to 1 L |

| Composite B vitamin Solution (LS03) | per L of Stock |
|---|---|
| Biotin | 20.0 mg |
| Folic acid | 20.0 mg |
| Pyridoxine hydrochloride | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Litre |

| Composite trace metal solution (LSO6) | per L of stock |
|---|---|
| Nitrilotriacetic Acid | 1.5 g |
| MgSO$_4$•7H$_2$O | 3.0 g |
| MnSO$_4$•H$_2$O | 0.5 g |
| NaCl | 1.0 g |
| FeSO$_4$•7H$_2$O | 0.1 g |
| Fe(SO$_4$)$_2$(NH$_4$)$_2$•6H$_2$O | 0.8 g |
| CoCl$_2$•6H$_2$O | 0.2 g |
| ZnSO$_4$•7H$_2$O | 0.2 g |
| CuCl$_2$•2H$_2$O | 0.02 g |
| AlK(SO$_4$)$_2$•12H$_2$O | 0.02 g |
| H$_3$BO$_3$ | 0.30 g |
| NaMoO$_4$•2H$_2$O | 0.03 g |
| Na$_2$SeO$_3$ | 0.02 g |
| NiCl$_2$•6H$_2$O | 0.02 g |
| Na$_2$WO$_4$•6H$_2$O | 0.02 g |

Media was prepared at pH 5.5 as follows. All ingredients with the exception of Cysteine-HCl were mixed in 400 ml distilled water. This solution was made anaerobic by heating to boiling and allowing it to cool to room temperature under a constant flow of N2 gas. Once cool, the Cysteine-HCl was added and the pH of the solution adjusted to 5.5 before making the volume up to 1000 ml; anaerobicity was maintained throughout the experiments.

Bacteria

*Clostridium autoethanogenum* were obtained from the German Resource Centre for Biological Material (DSMZ). The accession number given to the bacteria is DSMZ 19630.

Typical Continuous Culture in Bioreactor at Atmospheric Pressure for Inoculum

A five-liter bioreactor was filled with 4900 ml of the media LM33 without Composite B vitamin solution (LS03) or Cysteine-HCl and autoclaved for 30 minutes at 121° C. While cooling down, the media was sparged with N2 to ensure anaerobicity. Cysteine-HCl and Composite B vitamin solution (LS03) were then added. Anaerobicity was maintained throughout the fermentation. The gas was switched to 95% CO, 5% CO$_2$ at atmospheric pressure prior to inoculation with 100 ml of a *Clostridium autoethanogenum* culture. The bioreactor was maintained at 37° C. stirred at 200 rpm at the start of the culture. During the growth phase, the agitation was increased to 400 rpm. The pH was set to 5.5 and maintained by automatic addition of 5 M NaOH. Fresh anaerobic media was continuously added into the bioreactor to maintain a defined biomass and acetate level the bioreactor.

Example 1

Sterile serum bottles were purged three times with CO containing gas (20% CO2; 30% N2 and 3% H2 in CO) and then evacuated to a vacuum of −5 psi. 50 ml of active culture containing biomass, acetate and traces of ethanol under atmospheric pressure was transferred directly from a continuous bioreactor into the 234 ml serum bottle. The 184 ml headspace was then filled with the CO containing gas to 40 psia and incubated without shaking at the indicated temperature.

After 3, 6, 24 and 31 hours of incubation, a 2 mL sample from each serum vial was transferred into a new serum vial containing 50 mL of media (LM33) prepared in accordance with the above. The vials were filled with the CO containing gas to 40 psia and incubated at 37° C. for several days with constant agitation.

Growth of the inoculated vials was visually assessed at time intervals and −/+/++ were assigned to describe no growth, slight growth and dense growth respectively (see Table 1).

TABLE 1

Growth of inoculated *Clostridium autoethanogenum* culture following storage at various temperatures over 3, 6, 24 and 31 h.

| | Incubation time | | | | | | | | | | | |
|---|---|---|---|---|---|---|---|---|---|---|---|---|
| | 3 h | | | 6 h | | | 24 h | | | 31 h | | |
| Incubation | Days following inoculation | | | | | | | | | | | |
| temp | 0 | 1 | 2 | 0 | 1 | 2 | 0 | 1 | 2 | 0 | 1 | 2 |
| 4° C. | − | + | ++ | − | + | ++ | − | + | ++ | − | + | ++ |
| 14° C. | − | + | ++ | − | + | ++ | − | + | ++ | − | − | + |
| 24° C. | − | + | ++ | − | + | + | − | − | − | − | − | − |
| 37° C. | − | − | − | − | − | − | − | − | − | − | − | − |

The optimum temperature for production of products and microbial growth of *Clostridium autoethanogenum* is 37° C. At 37° C., the non shaken vials were either non-viable or had substantially reduced viability when used for inoculation after 3, 6, 24 and 31 hours. It is considered that without agitation, the active microbial culture rapidly depletes the limited CO dissolved in the liquid nutrient medium. The excess carbon monoxide in the headspace may have limited transfer into the liquid nutrient medium. However, in the absence of agitation, it is expected there will be a CO gradient, wherein the uppermost surface of the liquid nutrient medium may have a relatively high CO concentration, but this will decrease down through the medium. In the absence of agitation, the microbial cells will settle to the bottom of the vial, where they will be substantially starved of substrate and will rapidly decrease in viability. Subsequently, the deteriorated or dead culture is unsuitable for inoculation.

On reducing the temperature of the stored culture to 24° C., the microbial culture remained substantially viable for inoculation of a bioreactor for over 3 h. At 14° C., the microbial culture remained substantially viable following storage for 3 h, 6 h and 24 h. Following 31 h storage, the microbial culture remained viable, but took longer to grow following inoculation. At 4° C., the microbial culture remained viable following storage over all times investigated.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of sustaining viability of a microbial culture of a carboxydotrophic bacterium in a continuous fermentation process, the method comprising: providing a gaseous substrate comprising CO as the sole carbon source to a bioreactor comprising a fermentation broth comprising a culture of said bacterium suspended in a liquid nutrient medium; fermenting the gaseous substrate to alcohols and acids at an optimum operating temperature; monitoring the CO concentration in the fermentation broth; and when the CO concentration is determined to be limiting lowering the temperature of the fermentation broth below the optimum operating temperature such that viability of the bacterium is maintained, where the CO is determined to be limited when the rate of transfer of CO into the fermentation broth is less than the uptake of CO by the culture of the bacterium.

2. The method of claim 1 where the culture is maintained at a temperature of at least 5° C. below the optimum operating temperature.

3. The method of claim 1 where the culture is maintained at a temperature of at least 10° C. below the optimum operating temperature.

4. The method of claim 1 further comprising increasing the temperature of the fermentation broth to its optimum operating temperature in response to the CO concentration no longer being limiting.

5. The method of claim 1 where the culture is maintained at a temperature below the optimum operating temperature for a time of at least 3 hours.

6. The method of claim 1 where the carboxydotrophic bacterium is selected from the group consisting of Clostridium, Moorella, Pyrococcus, Eubacterium, Desulfobacterium, Carboxydothermus, Acetogenium, Acetobacterium, Acetoanaerobium, Butyribaceterium and Peptostreptococcus.

7. The method of claim 6, wherein the carboxydotrophic bacterium is *Clostridium autoethanogenum*.

8. A method of transporting a viable microbial culture of a carboxydotrophic bacterium comprising: transferring a fermentation broth comprising said bacterium, suspended in a liquid nutrient medium and at the bacterium's optimum operating temperature, from a bioreactor to a transportation vessel; pressurizing the transportation vessel with a gaseous substrate comprising CO; lowering the temperature of the vessel below the bacterium's optimum operating temperature; transporting the vessel to a remote location; the bacterium characterized in that it is capable of fermenting a gaseous substrate comprising CO as the sole carbon source to alcohols and acids.

9. The method of claim 8 where the temperature is lowered to at least 5° C. below the optimum operating temperature.

10. The method of claim 8 where the microbial culture is stirred during transport.

11. The method of claim 8 further comprising increasing the temperature of the transportation vessel at the remote location to the optimum operating temperature of the bacterium and inoculating a bioreactor with the microbial culture.

12. The method of claim 8 further comprising inoculating a bioreactor with the microbial culture at the remote location and increasing the temperature of the bioreactor to the optimum operating temperature of the bacterium.

13. The method of claim 8 where the carboxydotrophic bacterium is selected from the group consisting of Clostridium, Moorella, Pyrococcus, Eubacterium, Desulfobacterium, Carboxydothermus, Acetogenium, Acetobacterium, Acetoanaerobium, Butyribaceterium and Peptostreptococcus.

14. The method of claim 13 where the carboxydotrophic bacterium is *Clostridium autoethanogenum*.

15. A method of storing a viable microbial culture of a carboxydotrophic bacterium comprising: transferring a microbial culture comprising said bacterium, suspended in a liquid nutrient medium and at the bacterium's optimum operating temperature, to a storage vessel; pressurizing the storage vessel with a gaseous substrate comprising CO; lowering the temperature of the storage vessel below the optimum operating temperature of the bacterium; storing the microbial culture for a selected period of time; the bacterium characterized in that it is capable of fermenting the gaseous substrate comprising CO as the sole carbon source to alcohols and acids.

16. The method of claim 15 where the culture is stored at a temperature at least 5° C. below the optimum operating temperature.

17. The method of claim 15 where the culture is stored at a temperature of at least 10° C. below the optimum operating temperature.

18. The method of claim 15 where the culture is stored at a temperature below the optimum operating temperature for a time of at least 3 hours.

19. The method of claim 15 where the carboxydotrophic bacterium is selected from the group consisting of Clostridium, Moorella, Pyrococcus, Eubacterium, Desulfobacterium, Carboxydothermus, Acetogenium, Acetobacterium, Acetoanaerobium, Butyribaceterium and Peptostreptococcus.

20. The method of claim 19, wherein the carboxydotrophic bacterium is *Clostridium autoethanogenum*.

* * * * *